(12) United States Patent
Khalaj et al.

(10) Patent No.: US 11,931,066 B2
(45) Date of Patent: Mar. 19, 2024

(54) DIRECTLY CONNECTED SMART INVASIVE MEDICAL DEVICE ASSEMBLY

(71) Applicant: Avent, Inc., Alpharetta, GA (US)

(72) Inventors: Steve S. Khalaj, Laguna Hills, CA (US); Marc Comtois, Irvine, CA (US); Sung H. Lee, Suwanee, GA (US); Samin Askarian, Irvine, CA (US)

(73) Assignee: Avent, Inc., Alpharetta, GA (US)

( * ) Notice: Subject to any disclaimer, the term of this patent is extended or adjusted under 35 U.S.C. 154(b) by 141 days.

(21) Appl. No.: 17/184,657

(22) Filed: Feb. 25, 2021

(65) Prior Publication Data

US 2022/0265313 A1    Aug. 25, 2022

(51) Int. Cl.
*A61B 17/34* (2006.01)
*A61B 17/00* (2006.01)
*A61B 90/00* (2016.01)

(52) U.S. Cl.
CPC .......... *A61B 17/3403* (2013.01); *A61B 90/08* (2016.02); *A61B 2017/00424* (2013.01); *A61B 2017/00429* (2013.01); *A61B 2017/00477* (2013.01); *A61B 2017/3413* (2013.01); *A61B 2090/0811* (2016.02)

(58) Field of Classification Search
CPC ...... A61B 2017/3413; A61B 5/150519; A61B 8/12; A61M 5/32; A61M 25/0097
See application file for complete search history.

(56) References Cited

U.S. PATENT DOCUMENTS

| | | | | |
|---|---|---|---|---|
| 5,947,905 A | * | 9/1999 | Hadjicostis | A61B 8/12 600/463 |
| 2006/0106315 A1 | * | 5/2006 | Edens | A61B 17/3417 600/461 |
| 2014/0321244 A1 | | 10/2014 | Lee | |
| 2015/0182194 A1 | * | 7/2015 | Bruestle | G01S 15/8915 600/459 |
| 2016/0302772 A1 | * | 10/2016 | Cummins | A61B 8/4494 |
| 2016/0374710 A1 | | 12/2016 | Sinelnikov et al. | |
| 2017/0020562 A1 | * | 1/2017 | Erkamp | A61M 25/0108 |

(Continued)

FOREIGN PATENT DOCUMENTS

| | | | |
|---|---|---|---|
| WO | WO-2019108725 A1 | * | 6/2019 |
| WO | WO 2020/220033 A1 | | 10/2020 |
| WO | WO 2021/028154 A1 | | 2/2021 |

OTHER PUBLICATIONS

International Search Report and Written Opinion for PCT/US2022/016289, dated Jul. 22, 2022, 18 pages.

*Primary Examiner* — Colin T. Sakamoto
*Assistant Examiner* — Tommy T Ly
(74) *Attorney, Agent, or Firm* — Dority & Manning, P.A.

(57) ABSTRACT

An invasive medical device assembly includes an invasive medical device and a hub housing configured to surround a portion of the invasive medical device. The invasive medical device may be a needle or other invasive medical device, and the hub housing may be configured to surround a hub of the invasive medical device. In one aspect, the invasive medical device may include a transducer. The hub housing can include at least one integrated circuit embedded therein that is configured to contact the external surface of the needle to electrically connect the transducer to a power source. The hub housing can be configured to provide an ergonomic handle for a user.

8 Claims, 4 Drawing Sheets

(56) References Cited

U.S. PATENT DOCUMENTS

| | | |
|---|---|---|
| 2017/0127915 A1* | 5/2017 | Viebach ............... A61B 1/0057 |
| 2018/0264519 A1* | 9/2018 | Sudol ................... H05K 3/3421 |
| 2018/0289399 A9 | 10/2018 | McGahan et al. |
| 2019/0374162 A1 | 12/2019 | Ofek et al. |
| 2020/0205779 A1 | 7/2020 | Khalaj et al. |

* cited by examiner

DIRECTLY CONNECTED SMART INVASIVE MEDICAL DEVICE ASSEMBLY

FIELD OF THE INVENTION

The subject matter of the present invention relates generally to invasive medical device assemblies for use in, for example, nerve block procedures, and more particularly, an invasive medical device assembly with improved ergonomic handling and improved electrical connection to a power source.

BACKGROUND

Detection of anatomical objects using medical imaging is an essential step for many medical procedures, such as regional anesthesia nerve blocks, and is becoming the standard in clinical practice to support diagnosis, patient stratification, therapy planning, intervention, and/or follow-up. Various systems based on traditional approaches exist for anatomical detection and tracking in medical images, such as computed tomography (CT), magnetic resonance (MR), ultrasound, and fluoroscopic images.

For example, ultrasound imaging systems utilize sound waves with frequencies higher than the upper audible limit of human hearing. Further, ultrasound imaging systems are widely used in medicine to perform both diagnostic and therapeutic procedures. In such procedures, sonographers perform scans of a patient using a hand-held probe or transducer that is placed directly on and moved over the patient.

Certain ultrasound systems may be used in combination with needles having active (i.e., electrically-powered) transducers, which require an electrical connection to a power source. Such needle assemblies typically route cabling from the power source, past the proximal end of the needle, through a lumen of the needle and to the transducer. However, when the cabling is routed through the needle lumen, a portion of the internal diameter of the needle is obstructed, thereby preventing fluid/medicine from flowing freely therethrough. Moreover, when the power source is connected to the needle at the proximal end of the needle, additional electrical connection sub-assemblies may be required to attach to the proximal end of the needle assembly, which may get in the way of a user's ability to precisely handle the needle assembly during a patient procedure.

Accordingly, the present disclosure is directed to an invasive medical device assembly with improved electrical connection to a power source that addresses the aforementioned issues.

Consequently, there is a need for an invasive medical device assembly having improved handling and electrical connection to a power source. In particular, a needle assembly with ergonomic features would also be useful.

SUMMARY

Objects and advantages of the invention will be set forth in part in the following description, or may be obvious from the description, or may be learned through practice of the invention.

The present invention is directed to an invasive medical device assembly. The assembly includes an invasive medical device having a proximal end and a distal end, the distal end adapted to be inserted into a patient. The assembly additionally includes a transducer mounted to an external surface of the invasive medical device. The assembly further includes a hub housing configured to receive the proximal end of the invasive medical device. The hub housing includes at least one integrated circuit embedded therein. The at least one integrated circuit is configured to contact the external surface of the invasive medical device to electrically connect the transducer to a power source.

In one particular embodiment, the at least one integrated circuit embedded in the hub housing can include a molded interconnect device (MID).

In another embodiment, the at least one integrated circuit embedded in the hub housing can be configured to electrically connect the invasive medical device to the power source via a coaxial cable. Moreover, the at least one integrated circuit can include a first conductive region and a second conductive region, the first conductive region configured to electrically connect a first conductor of the coaxial cable to the invasive medical device, and the second conductive region configured to electrically connect a second conductor of the coaxial cable to the invasive medical device.

In an additional embodiment, the invasive medical device can further include at least one conductive element extending from the transducer to the proximal end electrically connecting the transducer to the at least one integrated circuit of the hub housing. Moreover, the at least one conductive element can include at least one of an electrical trace printed on the external surface of the invasive medical device via an additive manufacturing process, a flexible printed circuit board, an electrically conductive cable, or a combination thereof.

In a further embodiment, the hub housing can enclose a portion of the invasive medical device. Moreover, the hub housing can further include a port configured to receive a cable to electrically connect the at least one integrated circuit to the power source.

In yet another embodiment, the hub housing can include a concave seat configured to receive a portion of the invasive medical device. Moreover, the concave surface can include at least a portion of the at least one integrated circuit.

In one more embodiment, the invasive medical device can be a needle, a catheter, a stylet, a punch, or an introducer.

The present invention is further directed to a needle assembly. The needle assembly includes a needle having a proximal end and a distal end, the distal end adapted to be inserted into a patient, the proximal end having a hub. The needle assembly further includes a hub housing having a first grip surface, a second grip surface, a peripheral surface extending between the first grip surface and the second grip surface, and a finger guide extending from the peripheral surface. The hub housing is configured to provide an ergonomic handle for a user.

In one particular embodiment of the needle assembly, the hub housing can include a longitudinal axis extending from a proximal end to a distal end, wherein the hub housing is asymmetrical across the longitudinal axis.

In another embodiment, the hub housing can include a vertical axis extending therethrough, wherein the hub housing can be symmetrical about the vertical axis.

In a further embodiment, the first grip surface and/or the second grip surface may include an anti-slip three-dimensional texture. Further, the anti-slip three-dimensional texture can include at least one convex ridge.

In yet another embodiment, the hub housing can further include a cable port.

In an additional embodiment, the hub housing can further include a needle direction indicator configured to indicate an orientation of a bevel of the needle. Moreover, the needle direction indicator can be disposed on the peripheral surface or the finger guide. Further, the needle direction indicator can include a protrusion from the peripheral surface or the finger guide. Moreover, the needle direction indicator can include an arrow pointing in the orientation of the bevel of the needle.

In still another embodiment, the hub housing can have a first portion and a second portion, wherein the second portion is overmolded over the first portion and the needle hub. Moreover, the first portion can include a body comprising a first concave seat configured to receive the needle hub and a second concave seat configured to receive a needle cannula of the needle. Further, the second portion can be configured to enclose the needle hub and the at least one integrated circuit within the hub housing.

In one more embodiment, the needle can have a transducer mounted to an external surface of the needle; and the body of the hub housing can have at least one integrated circuit embedded therein, the at least one integrated circuit being configured to contact the external surface of the needle to electrically connect the transducer to a power source.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

As used herein, terms of approximation, such as "about," "approximately," or "generally," includes values within ten percent (10%) greater or less than the stated value are included within the disclosed embodiment. When used in the context of an angle or direction, such terms include within ten degrees greater or less than the stated angle or direction. For example, "generally vertical" includes directions within ten degrees of vertical in any direction, e.g., clockwise or counter-clockwise. Further, when a plurality of ranges are provided, any combination of a minimum value and a maximum value described in the plurality of ranges are contemplated by the present invention. For example, if ranges of "from about 20% to about 80%" and "from about 30% to about 70%" are described, a range of "from about 20% to about 70%" or a range of "from about 30% to about 80%" are also contemplated by the present invention.

Generally speaking, the present invention is directed to an invasive medical device assembly including an invasive medical device, such as a needle, and a hub housing configured to surround a portion of the invasive medical device, such as a hub of the needle. As described in further detail below, the invasive medical device of the present invention further contemplates other invasive medical devices such as stylets, cannulas, punches, and/or other ultrasound location or position-tracked medical devices. The invasive medical device assembly may include a transducer mounted to an external surface of the invasive medical device. The invasive medical device assembly further includes a hub housing including at least one integrated circuit embedded therein configured to contact the external surface of the invasive medical device to electrically connect the transducer to a power source. The present inventors have found that the invasive medical device assembly of the present invention enables direct electrical connection between the invasive medical device and a power source without the use of any extraneous subassemblies. The hub housing of the invasive medical device assembly of the present invention has an ergonomic form including a first grip surface and a second grip surface configured to be held by two fingers, and a finger guide extending from a periphery of the hub housing configured for a user's finger to guide the orientation of the invasive medical device. The present inventors have found that the ergonomic form of the hub housing can enable improved gripping and control of the invasive medical device assembly with reduced slippage even when used by a gloved user. Moreover, the present inventors have found that the finger guide can enable more precise guided control of the orientation and positioning of the invasive medical device, e.g., during a pain management procedure in which the needle may need to be driven into a deep tissue area.

The specific features of the invasive medical device assembly of the present invention may be better understood with reference to FIGS. 1-9. A needle is illustrated in FIGS. 1-3 and 7-9 as an example of an invasive medical device and is not intended to limit the present disclosure to needles. It should be understood that the present disclosure may be used with any of several various types of invasive medical devices. As an example of an invasive medical device, the present disclosure may be useful for providing a direct electrical connection between a power source and any smart invasive medical device, e.g., needles, catheters, stylets, tissue punches. Thus, it is to be understood that the features of the present disclosure may be incorporated into any of a variety of invasive medical devices. It should be understood that "invasive," as used herein, means 'involving entry into a living body,' such as by incision or by insertion of an instrument having contact with the mucosa, requiring skin break, or contact with an internal body cavity beyond a natural or artificial body orifice. For example, deep palpation and percussion are non-invasive but insertion of a medical device into the digestive tract or through an incision is invasive.

Figure 1:
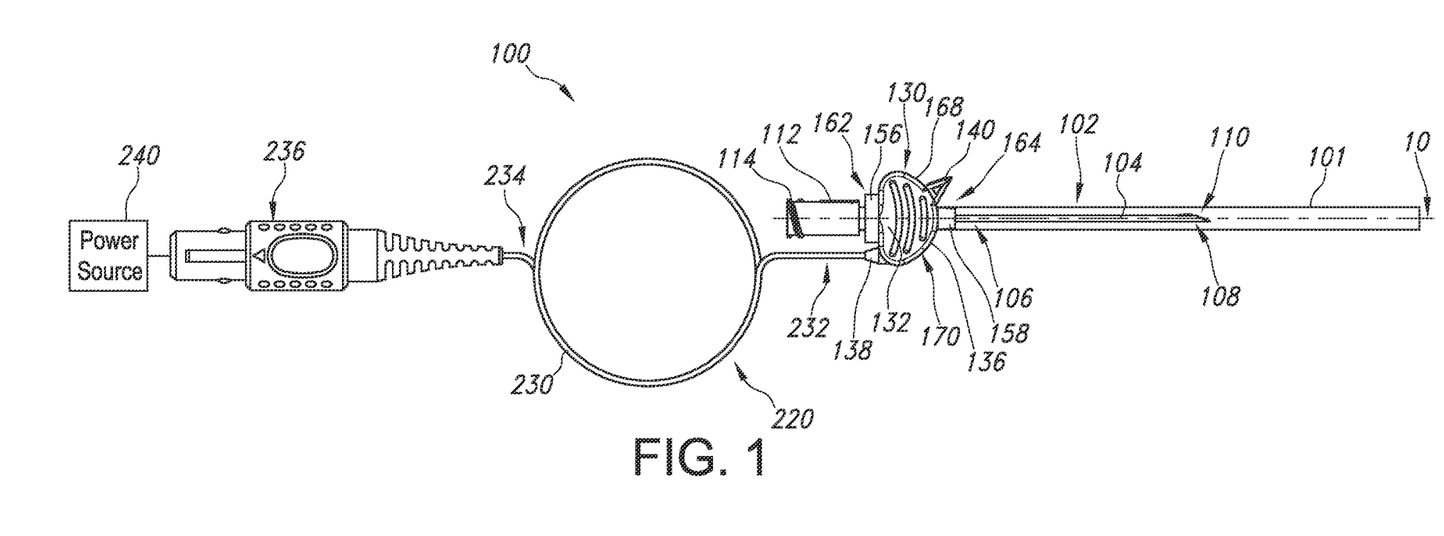
FIG. 1 illustrates a side view of an invasive medical device assembly according to one particular embodiment of the present invention in which the invasive medical device is illustrated as a needle.

Referring now to FIG. 1, one embodiment of an invasive medical device assembly 100 of the present invention is shown. The invasive medical device assembly 100 as illustrated includes a needle 102 as an exemplary, non-limiting invasive medical device. The needle 102 has a needle cannula 104 extending from a proximal end 106 to a distal end 108. The distal end 108 is adapted to be inserted into a patient, e.g., into the patient's skin. The distal end 108 of the needle 102 can include a bevel 110 as shown, or one or more features of any other needle style, such as a blunt tip, tapered tip, Tuohy needle, etc. The needle 102 can include a needle guard 101, e.g., a sheath surrounding the needle cannula 104, configured to protect the integrity of the distal end 108 of the needle and prevent a user from accidental puncture or injury. At the proximal end 106, the needle 102 may include a hub 112. The hub 112 can include or be connected to a fluid connector 114 such as a female or male Luer connector. The invasive medical device assembly 100 further includes a hub housing 130 that can be adapted to provide an ergonomic grip for a user of the invasive medical device assembly 100, as will be described in further detail below.

Figure 8:
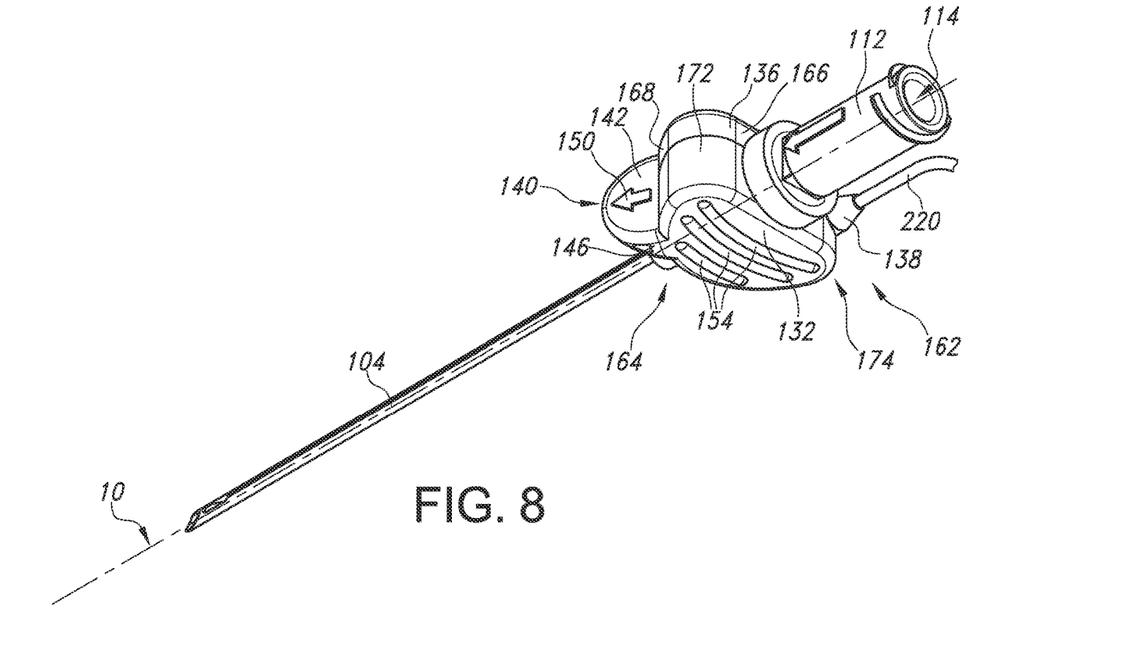
FIG. 8 illustrates a perspective view of the hub housing of the invasive medical device assembly of FIG. 1.
Figure 9:
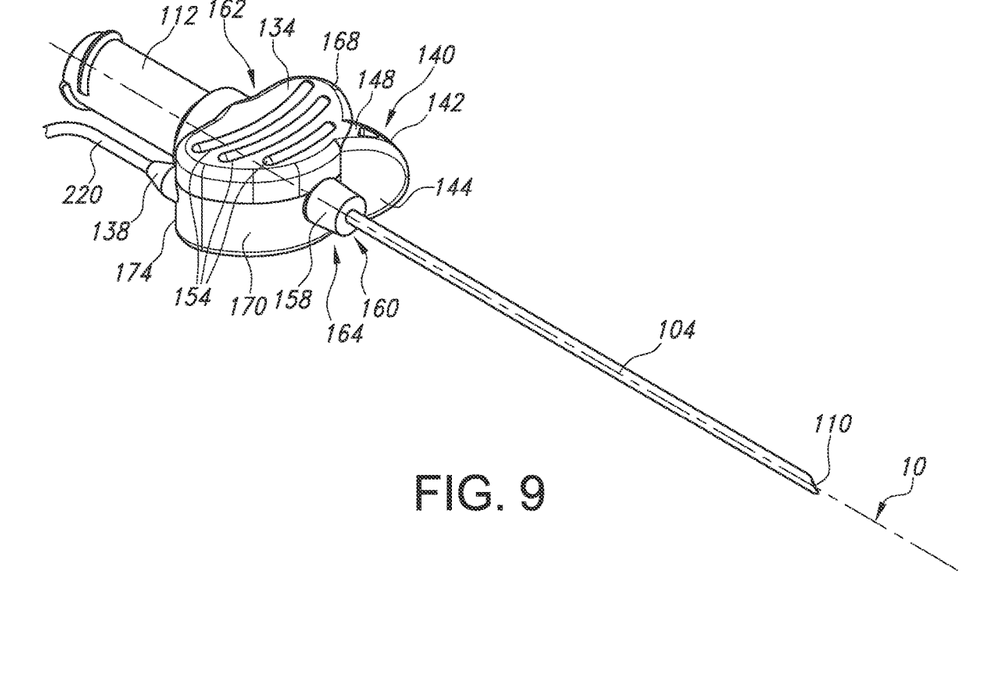
FIG. 9 illustrates a perspective view of the hub housing and needle of the invasive medical device assembly of FIG. 1.

As shown in FIGS. 1 and 8-9, the hub housing 130 extends from a proximal end 162 to a distal end 164. A first grip surface 132 and a second grip surface 134 (see FIG. 9) each extend from the proximal end 162 to the distal end 164 of the hub housing 130. The second grip surface 134 can be disposed opposite to the first grip surface 132. For instance, the first grip surface 132 and the second grip surface 134 can be disposed generally parallel to each other. A peripheral surface 136 extends from the first grip surface 132 to the second grip surface 134 to connect the first grip surface 132 and the second grip surface 134. As shown in FIGS. 8-9, the peripheral surface 136 includes a proximal peripheral surface 166 extending along the proximal end 162 of the hub housing 130 from the first grip surface 132 to the second grip surface 134. The peripheral surface 136 further includes two lateral peripheral surfaces 168 and 170. Each lateral peripheral surface 168, 170 extends between the first grip surface 132 and the second grip surface 134 from the proximal end 162 to the distal end 164 of the hub housing 130. For instance, the lateral peripheral surface 168 may be an upper lateral peripheral surface disposed above a longitudinal axis 10, and the lateral peripheral surface 170 may be a lower lateral peripheral surface disposed below the longitudinal axis 10. The proximal peripheral surface 166 may extend generally perpendicular to the longitudinal axis 10. The hub housing 130 may have a rounded corner 172 where the proximal peripheral surface 166 and the upper lateral peripheral surface 168 meet, and another rounded corner 174 where the proximal peripheral surface 166 and the lower lateral peripheral surface 170 meet.

The hub housing 130 may be adapted to be held within two fingers of a user's hand, e.g., between a thumb and a finger of the user's hand. Referring still to FIGS. 1-2 and 8-9, the first grip surface 132 and/or the second grip surface 134 may include a three-dimensional texture adapted to improve the surface for gripping by a user, e.g., to reduce or prevent slippage. For instance, as shown in FIGS. 8-9, there can be one or more anti-slip ridges 154 disposed on the first grip surface 132 and/or the second grip surface 134. The anti-slip ridges 154 can extend in a direction from the upper lateral peripheral surface 168 to the lower lateral peripheral surface 170, i.e., generally perpendicular to or extending across the longitudinal axis 10. Additionally or alternatively, the three-dimensional texture can include ridges extending along, i.e., generally parallel to, the longitudinal axis 10, protrusions and/or indentations having a rounded or polygonal shape, wavy texture, a rough surface texture, or any other three-dimensional texture adapted to improve the ability for a user to maintain a grip on the first grip surface 132 and/or the second grip surface 134.

The hub housing 130 further includes a finger guide 140 protruding from the upper lateral peripheral surface 168. The finger guide 140 is adapted to form a finger rest upon which a user may place their finger to guide the positioning of a needle 102. The finger guide 140 may have a generally triangular shape, as shown in FIGS. 1-2 and 8-9, or any other suitable shape adapted for a user to rest a finger on to guide the invasive medical device. As shown in FIGS. 8-9, the finger guide 140 includes an upper surface 142 upon which a user may rest their finger, a lower surface 144, a first side surface 146 adjacent to the first grip surface 132 and a second side surface 148 adjacent to the second grip surface 134.

As shown in FIG. 1, the hub housing 130 is asymmetrical across the longitudinal axis 10. In particular, the finger guide 140 protrudes from the upper lateral peripheral surface 168, which is disposed above the longitudinal axis 10. Additionally, the cable port 138 protrudes from the proximal peripheral surface 166 below the longitudinal axis 10. However, as shown in FIGS. 8-9, the hub housing 130 is generally symmetrical about a transverse plane (not shown) extending vertically through the hub housing from the proximal end 162 to the distal end 164 of the hub housing 130. In other words, the side of the hub housing 130 comprising the first grip surface 132 and the side of the hub housing 130 comprising the second grip surface 134 are generally symmetrical to each other. In such a manner, the ergonomic form of the hub housing 130 may be easily handled by a right-handed user or a left-handed user without prejudice.

Figure 3:
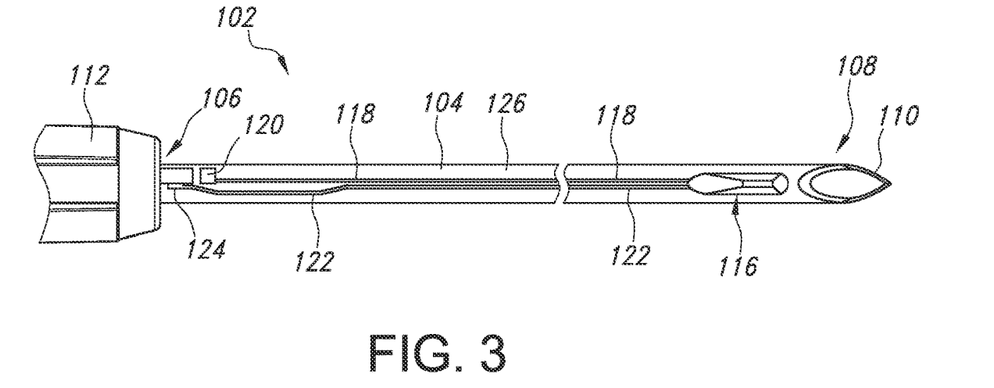
FIG. 3 illustrates a bottom view of a smart needle according to the present invention.

Turning now to FIG. 3, in some embodiments, the invasive medical device assembly 100 may include one or more transducer(s) 116. The transducer(s) 116 may be implemented to enable ultrasound location or position tracking of the invasive medical device, e.g., needle 102. The one or more transducer(s) 116 can be mounted to the invasive medical device, e.g., an external surface 126 of the needle 102 as shown in FIG. 3. For example, the transducer(s) 116 may be mounted at the distal end 108 of the invasive medical device such as the needle 102, to enable tracking of the placement of the distal end 108 within a patient's body during a procedure. For instance, the transducer(s) 116 may be disposed adjacent to the bevel 110 or in a bevel up orientation the needle 102 as shown in FIG. 3. It should be understood, however, that the transducer 116 may be mounted at any suitable location on the external surface 126 of the needle cannula 104.

In addition, the transducer(s) 116 may be any suitable transducer now known or later developed in the art. For example, in one embodiment, the transducer(s) 116 may be a piezoelectric (PZT) transducer. Alternatively, the transducer(s) 116 may be a capacitive micromachined ultrasonic (CMUT) transducer. In yet another embodiment, the transducer(s) 116 may also include Polydimethylsiloxane (PDMS) transducers and/or photoacoustic transducers.

Figure 4:
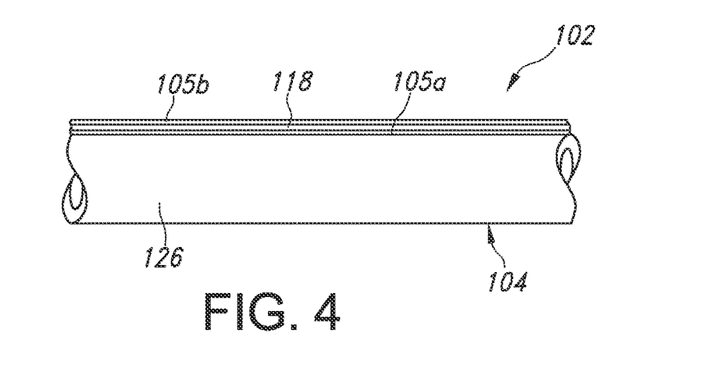
FIG. 4 illustrates a detailed view of a portion of the needle of FIG. 3, particularly illustrating an electrical trace printed onto an external surface of the needle.

Referring now to FIGS. 3 and 4, an external surface 126 of the invasive medical device, e.g., needle cannula 104, may be coated, at least in part, with a first coating material, e.g., an electrically insulating material. Further, as shown, the invasive medical device, i.e., needle 102, of the assembly 100 may include at least one electrical trace, e.g., electrical traces 118 and 122, printed onto the insulated portion of the needle 102 from the proximal end 106 to the distal end 108, e.g., via an additive manufacturing process. As such, the electrical trace(s) 118, 122 are configured to electrically connect the needle transducer 116 to a power source, e.g., the power source 240 as shown in FIG. 1. In addition, another insulating material may be wrapped around the printed traces 118, 122 to form a second insulating layer 105b to shield the electrical trace(s) 118, 122 from the patient. Thus, in such embodiments, the external surface 126 of the needle cannula 104 can be coated (such as by vacuum deposition, spraying, or dipping) with insulating material (such as parylene or polyimide) to form a first insulating layer 105a and the conductive electrical traces 118, 122 can subsequently be placed over the first insulating layer 105a (by deposition or conductive film, such as gold or copper). In addition, as mentioned, another insulation layer, i.e., second insulating layer 105b, can then be used to cover the electrical trace(s) 118, 122 and the first insulating layer 105a. It should be further understood that the insulation layer(s) 105a, 105b may also be used to insulate the needle cannula 104 from any other means of electrically connecting the transducer 116 to the power source 240, e.g., by a flexible printed circuit board, electrical cable such as coaxial cable, enameled wire, or the like.

In certain embodiments, the additive manufacturing process may include, for example, directed energy deposition, direct laser deposition, aerosol deposition, or any other suitable additive manufacturing technique. By using additive manufacturing, the electrical trace(s) 118, 122 can be printed at the distal end 108 of the needle 102 in thin layers so as not to disturb the overall efficacy of the needle 102 in puncturing the necessary tissue of the patient. For example, in one embodiment, each of the electrical trace(s) 118, 122 may have a predetermined thickness ranging from about 0.01 millimeters (mm) to about 0.05 mm.

The invasive medical device assembly 100 of the present invention may include an electrical connection between the power source 240 and the invasive medical device, e.g., needle 102. For instance, as shown in FIGS. 2 and 5-7, the hub housing 130 may include one or more integrated circuits embedded therein that are configured to electrically connect with the electrical traces 118, 122 of the needle 102 of FIGS. 3-4.

Figure 5:
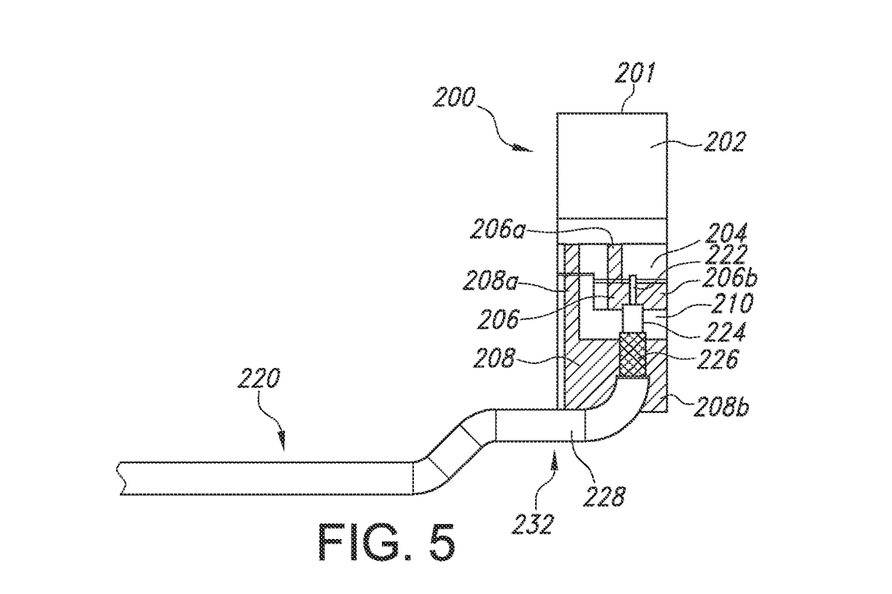
FIG. 5 illustrates a top view of an electrical connection assembly for a needle hub housing according to one particular embodiment of the present invention.

Referring to FIG. 5, the one or more integrated circuits in the hub housing 130 may include a molded interconnect device (MID) 200 (also known as a mechatronic integrated device), e.g., a three-dimensional molded interconnect device (3D-MID) configured to electrically connect the power source 240 to the invasive medical device, e.g., needle 102. The MID 200 has a body 201 which may be formed from an injection-molded thermoplastic with integrated electronic circuit traces formed by selective metallization. For instance, the electronic circuit traces may be structured by laser structuring, additive manufacturing (printing), or any other suitable method to form conductive traces on the body 201. The conductive traces may be formed by one or more layers of conductive metals, e.g., successive layers of copper, nickel and gold. Other conductive compounds, including but not limited to silver, platinum, graphite, and conductive polymers, may also be used to form the conductive traces. As will be described in further detail below, the conductive traces of the MID 200 may be formed into one or more electrical contact regions configured to directly electrically connect the power source 240 to the invasive medical device, e.g., needle 102, without any additional subcomponents.

The body 201 of the MID 200 includes at least an upper surface 202. The upper surface 202 can include a concave seat 204 in which the invasive medical device, for instance the cannula 104 of the needle 102, can be placed. The MID 200 may include one or more electrical contact regions, e.g., a first electrical contact region 206 and a second electrical contact region 208, that include conductive particles and are configured to form electrical connections with the invasive medical device, e.g., needle 102. The electrical contact regions 206 and 208 may at least partially overlap the concave seat 204 such that the invasive medical device, e.g., needle 102, may contact the electrical contact regions 206 and 208 when the invasive medical device, e.g., needle 102, is seated on the body 202 of the MID 200. An insulating region 210 may be disposed between the first electrical contact region 206 and the second electrical contact region 208. The insulating region 210 may be formed from non-conductive material.

Although the MID 200 is illustrated as a drop-in part of the hub housing 130, the present invention further contemplates the MID 200 being formed integrally with the hub housing 130. For instance, the MID 200 could be molded to form the entire first portion 180 of the hub housing 130 in one piece as described in further detail below in a manner that integrally includes the electrical contact regions 206 and 208.

As shown in FIGS. 1-2 and 5-7, the power source 240 may be connected to the hub housing 130, e.g., via the MID 200, in the form of a coaxial cable 220. The coaxial cable 220 may be formed from a first conductor, e.g., an inner copper wire 222, an insulating layer 224 surrounding the copper wire 222, a second conductor, e.g., braided metal layer 226 surrounding the insulating layer 224, and an external insulating jacket 228. The coaxial cable 220 may extend along a length 230 from a distal end 232 (i.e., configured to electrically connect with the smart invasive medical device, e.g., needle 102) to a proximal end 234 and terminate in a coaxial cable connector 236 at the proximal end 234 of the cable 220.

For instance, the first electrical contact region 206 can be configured to electrically connect between the power source 240, e.g., a coaxial cable 220, and the first electrical trace 118 of the needle 102. In particular, the first electrical contact region 206 may include a medical device contact portion 206a and a power source contact portion 206b. The medical device contact portion 206a can be configured to contact a first electrical connection 120 of the first electrical trace 118 of the needle 102. The power source contact portion 206b can be configured to electrically connect with the power source 240, e.g., via the first conductor, the inner copper wire 222 of the coaxial cable 220.

Similarly, the second electrical contact region 208 can be configured to electrically connect between the power source 240, e.g., a coaxial cable 220, and the second electrical trace 122 of the needle 102. In particular, the second electrical contact region 208 may include a medical device contact portion 208a and a power source contact portion 208b. The medical device contact portion 208a can be configured to contact a second electrical connection 124 of the second electrical trace 122 of the needle 102. The power source contact portion 208b can be configured to electrically connect with the power source 240, e.g., via the second conductor, the braided metal layer 226 of the coaxial cable 220.

In some aspects of the invention, the medical device contact portions 206a and 208a may each extend from the power source contact portions 206b and 208b of the first electrical contact region 206 and second electrical contact region 208, respectively. For instance, as shown in FIG. 5, the power source contact portion 206b of the first electrical contact region 206 can have a shape, e.g., a rectangular shape, and the needle contact portion 206a can extend from a portion of the shape of the power source contact portion 206b. As shown in FIG. 5, the medical device contact portion 206a can have a shape, e.g., a rectangular shape, extending from one side of the power source contact portion 206b. Additionally, the medical device contact portions 206a and 208a may each have a different size than the power source contact portions 206b and 208b of the first electrical contact region 206 and second electrical contact region 208, respectively. As shown in FIG. 5, the medical device contact portions 206a and 208a may each be smaller in size than the power source contact portions 206b and 208b.

Figure 2:
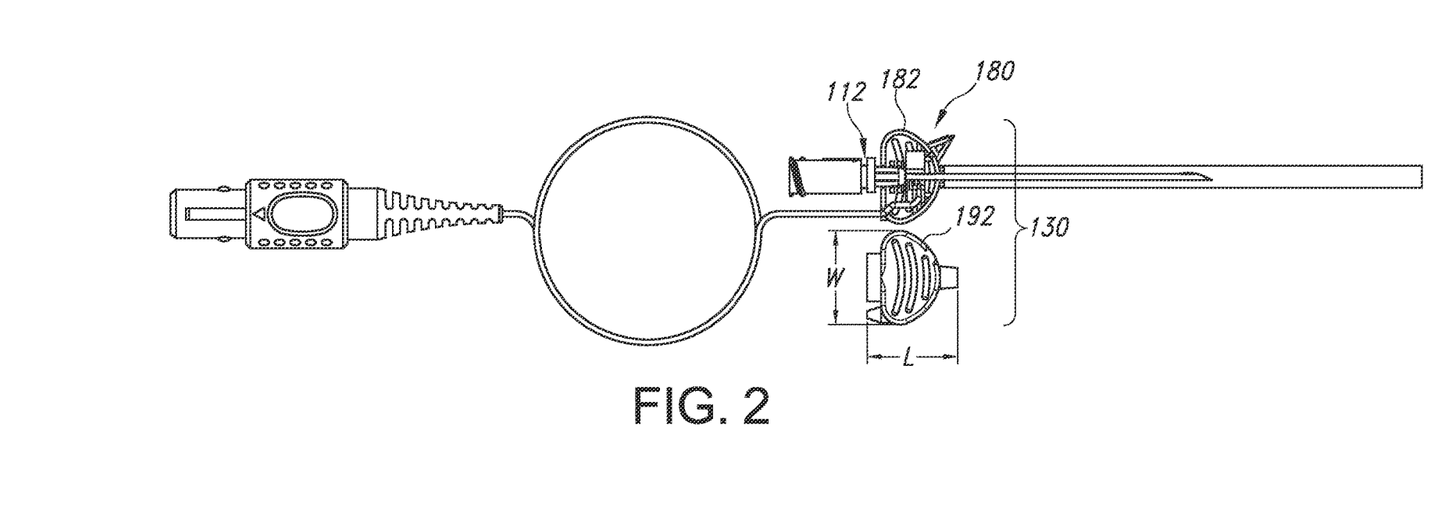
FIG. 2 illustrates a side view of the invasive medical device assembly of FIG. 1 having the first portion and the second portion of the hub housing dissembled.
Figure 6:
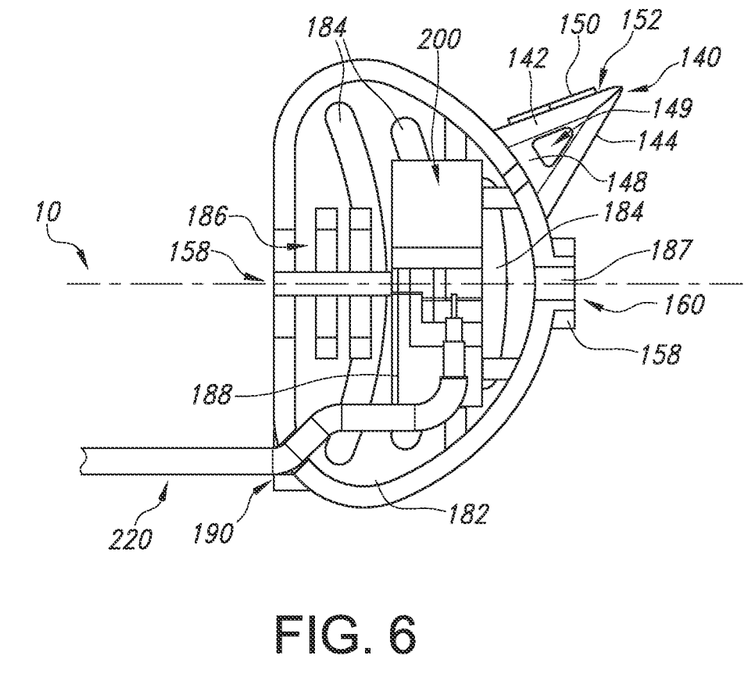
FIG. 6 illustrates the electrical connection assembly of FIG. 5 placed within a portion of the hub housing according to one particular embodiment of the present invention.
Figure 7:
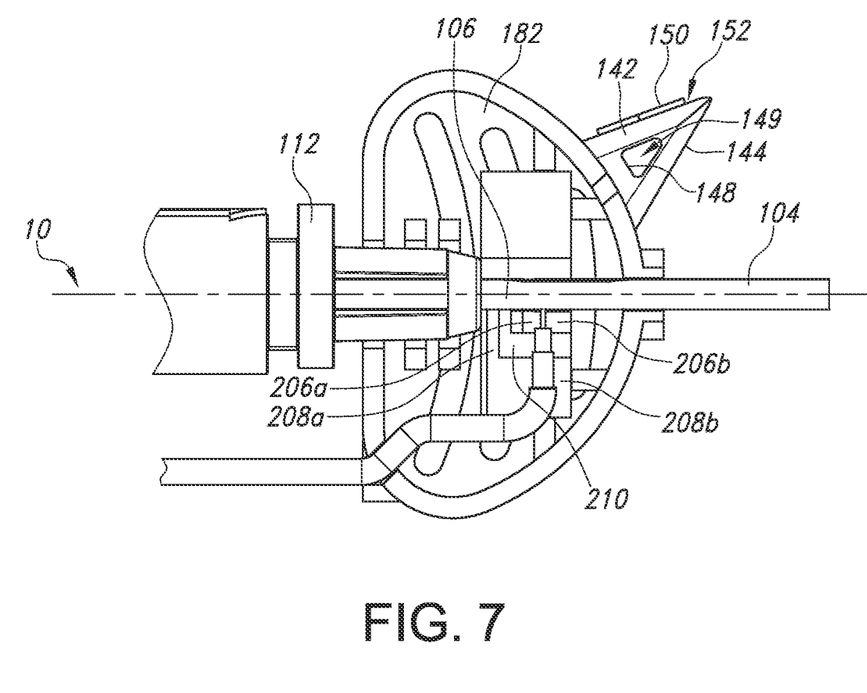
FIG. 7 illustrates the needle of FIG. 3 in place with the electrical connection assembly and hub housing of FIG. 6.

As shown in FIGS. 1-2 and 6-7, the MID 200, needle hub 112 and proximal end 106 of the invasive medical device, i.e., needle 102, and the distal end 232 of the coaxial cable 220 can be enclosed within the hub housing 130 to form a unitary invasive medical device assembly 100. As illustrated in FIGS. 2 and 6-7, the hub housing 130 may be formed from a first portion 180 and a second portion 192. The second portion 192 may be overmolded over the first portion 180. The first portion is formed by a body 182. The body 182 is configured to form a skeleton for the hub housing 130. The body 182 may include one or more openings 184. The one or more openings 184 can extend between the upper lateral peripheral surface 168 and the lower lateral peripheral surface 170 of the hub housing 130. The one or more openings 184 can be configured to prevent separation between the first portion 180 and the second portion 192 by increasing the surface area of the first portion 180 for contact with the overmolded second portion 192. The body 182 of the first portion 180 may be formed as a unitary structure, i.e., manufactured, e.g., by molding, as a single unitary piece. The body 182 may be formed from a thermoplastic material, e.g., polycarbonate or any other suitable thermoplastic material that can be formed into the shape of the body 182.

On an upper lateral edge of the body 182, the finger guide 140 extends from the body 182. (See FIG. 6.) For instance, as described above, the finger guide 140 may be integrally formed with the body 182, e.g., by injection molding as a unitary piece. The body 182 may include a finger guide opening 149, as shown in FIGS. 6 and 7. The finger guide opening 149 may be an opening in the body 182 formed between the upper surface 142 and the lower surface 144 of the finger guide 140. The finger guide opening 149 may extend from the first side surface 146 to the second side surface 148 of the finger guide 140. In such a manner, the finger guide opening 149 of the body 182 may be filled with a material as described in further detail below.

The body 182 includes a first concave seat 186 configured to receive the hub 112 of the needle 102. The first concave seat 186 may be disposed adjacent to the proximal lateral peripheral surface 166 of the hub housing 130 and terminate in a needle hub opening 156 in the proximal lateral peripheral surface 166 such that the needle hub 112 can extend through the proximal lateral peripheral surface 166. Optionally, the first concave seat 186 may be formed from a plurality of ribs extending generally perpendicular to the longitudinal axis 10, as shown in FIG. 6. Additionally, the body 182 further includes a second concave seat 187 configured to receive the cannula 104 of the needle 102. The second concave seat 187 may be disposed along the longitudinal axis 10 of the hub housing 130. For instance, the second concave seat 187 may be positioned between the upper lateral peripheral surface 168 and the lower lateral peripheral surface 170 such that the needle cannula 104 can extend through a needle cannula port 158 at the distal end 164 of the hub housing 130. The needle cannula port 158 may extend from the distal end 164 of the hub housing 130 generally at a point where the upper lateral peripheral surface 168 and the lower lateral peripheral surface 170 meet.

The body 182 further includes a recess 188 configured to receive the MID 200. For instance, the recess 188 can be adapted to match the size and shape, i.e., external dimensions, of the MID 200 such that the MID 200 fits securely within the recess 188. The recess 188 can be centered along the6longitudinal axis 10 extending between the proximal peripheral surface 166 and the distal end 164 of the hub housing 130. As described above, the body 201 of the MID includes a concave seat 204 (see FIG. 5) in which a portion of the invasive medical device, e.g., the needle cannula 204 can be placed. The recess 188 for the MID 200 may be positioned within the hub housing 130 such that the concave seat 204 may extend along the longitudinal axis 10 and aligns with the second concave seat 187 of the body 182. In such an arrangement, the needle 102 may be placed within the body 182 such that the needle hub 112 is seated within the first concave seat 186 and the needle cannula 104 extends from the needle hub 112 through the needle cannula opening 160 at the distal end 164 of the hub housing 130 and is seated within the concave seat 204 of the MID 200 and the second concave seat 187 of the body 182.

The body 182 further includes a concave cable recess 190 in which the coaxial cable 220 is configured to be placed. The concave cable recess 190 forms a portion of the cable port 138 of the hub housing 130. The concave cable recess 190 may be formed in the proximal peripheral surface 166 such that the coaxial cable 220 is configured to extend in an opposite direction from the distal end 108 of the needle cannula 104. As shown in FIGS. 5-6, the concave cable recess 190 may be disposed nearer to the lower lateral peripheral surface 170 compared to the first concave seat 186 for the needle hub 112. In such a configuration, the coaxial cable 220 is configured to extend in a proximal direction from the hub housing 130 and away from the grip surfaces 132, 134 and the finger guide 140 of the hub housing 130, thus reducing the likelihood of the coaxial cable 220 interfering with the user's handling of the hub housing 130 and placement of the needle 102 during a procedure.

Turning to FIGS. 1-2 and 8-9, the second portion 192 of the hub housing 130 may be overmolded over the body 182, MID 200, needle 102 and coaxial cable 220. In such a configuration, the needle 102, MID 200 and coaxial cable 220 may be enclosed or encapsulated within the hub housing 130. In this arrangement, the invasive medical device assembly 100 may be formed into a single functional unit, i.e., the MID 200, coaxial cable 220 and needle 102 may not be removed from the invasive medical device assembly 100 unless the invasive medical device assembly 100 is dissembled, broken or destroyed.

The second portion 192 of the hub housing 130 may be formed from a pliable material such as a thermoplastic elastomer and/or a thermoset rubber such as silicone. However, it is to be understood that any suitable over-mold material that that has a hardness less than or generally equal to the material of the body 182 of the first portion 180 of the hub housing 130 may be used. When such an elastomer or thermoset rubber is used, it can be a medical-compliant over-mold that adheres to various substrates, including the types of more rigid material used in the first portion 180 of the hub housing 130, noted above. This type of material has a rubber feel and soft touch and can optionally be clear or translucent. For instance, the material of the second portion 192 can be used in injection molding fabrication, as will be discussed in greater detail. The second portion 192 of the hub housing 130 also can be made of an opaque material, including materials that can possess preselected color characteristics. The second portion 192 of the hub housing 130 can provide a good gripping material for individuals who are handling and manipulating the hub housing 130 of the invasive medical device assembly 100 (e.g., surgeon, doctor, nurse, etc.). The second portion 192 of the hub housing 130 may also provide a resilient enclosure that permits the use of a more rigid first material for the first portion 180 of the hub housing 130 while protecting the first portion 180 from breakage, damage, slipperiness and other undesirable characteristics. For instance, protecting the first portion 180 may be particularly critical for protecting the direct electrical connections within the hub housing 130. The combination of the first portion 180 and the second portion 192 to form the hub housing 130 permits an organic shape that allows for ergonomic gripping of the hub housing 130 during use of the invasive medical device assembly 100 and enhances control and guidance of the invasive medical device 102, e.g., needle 102, by the user.

The cable port 138 may be formed as part of the second portion 192 of the hub housing 130. For instance, the cable port 138 may be formed by overmolding around the coaxial cable 220 extending from the first portion 180 of the hub housing 130. The cable port 138 may be in the form of a cylindrical-shaped overmold surrounding the coaxial cable 220 and extending in a proximal direction from the proximal peripheral surface 166. However, the cable port 138 may have any other shape or form that may be suitable for holding the coaxial cable 220 in place extending from the concave cable recess 190 of the first portion 180 of the hub housing 130, such as a cylindrical shape, three-dimensional prism (e.g., rectangular prism) or pyramid shape (e.g., triangular or rectangular pyramid), or any other geometric or non-geometric shape.

In a similar manner as the cable port 138 described above, both the needle hub port 156 and the needle cannula port 158 may be formed as part of the second portion 192 of the hub housing 130. For instance, the needle hub port 156 may be formed by overmolding the material of the second portion 192 around the needle hub 112 extending from the first concave seat 186 of the body 182 of the first portion 180. Similarly, the needle cannula port 158 may be formed by overmolding the material of the second portion 192 around the needle cannula 104 extending from the second concave seat 187 of the body 182 of the first portion 180. By surrounding the second portion 192 around the needle hub 112 and the needle cannula 104 at the hub port 156 and the cannula port 158, respectively, the needle 102 can be securely held in place in the hub housing 130. The needle hub port 156 and the needle cannula port 158 may each be in the form of a cylindrical shape surrounding the needle hub 112 and the needle cannula 104, respectively, or any other shape or form suitable for holding the needle 102 in place.

As shown in FIGS. 1 and 8-9, the first grip surface 132, the second grip surface 134, and the peripheral surfaces 166, 168, 170 of the hub housing 130 are formed by the second portion 192 of the hub housing 130. Moreover, the anti-slip ridges 154 may be formed in or on the first grip surface 132 and second grip surface 134 as part of the overmolded second portion 192. For instance, the anti-slip ridges 154 may correspond to, e.g., mirror or have the same shape and size as, the openings 184 in the body 182 of the first portion 180. However, at least a portion of the external surface of the hub housing 130 is formed from the body 182 of the first portion 180 and is configured to be exposed from and/or protrude from the second portion 192. The finger guide 140, which is formed as part of the body 182 of the first portion 180 as described above, is configured to protrude beyond the overmolded second portion 192. Put another way, the second portion 192 is configured to surround and abut the surfaces/sides 142, 144, 146, 148 of finger guide 140. However, in some aspects of the invention, the overmolded second portion 192 may be used to fill in the finger guide opening 149 of the finger guide 140. In another embodiment of the present invention, the finger guide 140 may be formed from the overmolded second portion 192.

As shown in at least FIG. 2, the hub housing 130 may have a maximum length L extending along the longitudinal axis 10, and a maximum width W extending perpendicular to the longitudinal axis. The maximum length L extends from a proximal end 162 of the hub housing 130, e.g., at a proximal end of needle hub port 156 and/or a proximal end of the cable port 138 (i.e., the elements of the hub housing 130 which protrude from the proximal peripheral surface 166 in a proximal direction) to a distal end 164 of hub housing 130, e.g., the needle cannula port 158 and/or the finger guide 140 (i.e., the elements of the hub housing 130 which protrude from the grip surfaces 132, 134 in a distal direction). In some particular embodiments, the needle hub port 156 and the proximal end of the cable port 138 may be aligned along the longitudinal axis 10. Similarly, in some embodiments, the opening 160 of the needle cannula port 158 and a tip of the finger guide 140 may be aligned along the longitudinal axis 10. In this arrangement, the hub housing 130 may have a compact configuration in which none of the protrusions (i.e., the needle hub port 156 and the cable port 138 on the proximal side and the needle cannula port 158 and the finger guide 140 on the distal side) extend beyond each other.

In some aspects of the present invention, the hub housing 130 includes an indicator 150 adapted to align with the bevel 110 of the needle 102 in order to indicate the orientation of the bevel 110 of the needle 102. The indicator 150 can be adapted to direct a user by sight and/or by touch in the direction the user wants the needle 102 to go in a bevel up orientation. For instance, the finger guide 140 may extend, i.e., be pointed, in the same direction as the bevel 110 in a bevel up orientation to form an indicator 150 of the orientation of the bevel 110. Additionally or alternatively, a visual or tactile indicator 150 may be disposed on the hub housing 130, e.g., on the finger guide 140. As shown in FIGS. 6-8, an indicator 150 may be disposed on the upper surface 142 of the finger guide 140 indicating the orientation of the bevel 110 of the needle 102. For instance, the indicator 150 can take the shape of an arrow pointing in the direction of the bevel 110, or any other suitable shape, letter, word, or marking suitable to guide the user in the orientation of the bevel 110 of the needle 102. The indicator 150 can be raised from a surface of the hub housing 130 or indented within a surface of the hub housing 130 along a ridge 152 (see FIGS. 6-7) outlining the indicator 150. For instance, in one particular embodiment, the indicator 150 can be formed from the overmolded second portion 192 of the hub housing 130 to protrude from the upper surface 142 of the finger guide 140.

Although not illustrated, the hub housing 130 of the present invention having a first grip surface 132 and a second grip surface 134 may be used with any needle, e.g., a needle without a transducer or electrical connection, to provide an ergonomic grip for improved handling of the needle. Similarly, the indicator 150 of the present invention indicating the orientation of the bevel 110 of a needle may be used with any needle or needle assembly. In particular, the present invention contemplates a needle assembly including a needle and a hub housing including a first grip surface 132 and a second grip surface 134, and optionally a finger guide 140, configured to enable improved handling and guiding of the orientation of the needle, particularly for guiding the orientation of the bevel of the needle. Moreover, the hub housing 130 and indicator 150 can be used with any invasive medical device that requires directional handling control by a user. For instance, the ergonomic hub housing 130 and indicator 150 of the present invention can be used with various types of catheters, stylets, introducers, tissue punches, and other invasive medical devices which are configured to be manually positioned by a user and/or which benefit from placement or insertion at a particular orientation.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. An invasive medical device assembly comprising:
an invasive medical device comprising a proximal end, a distal end, and an external surface, the distal end adapted to be inserted into a patient;
a transducer mounted to the external surface of the invasive medical device;
a hub housing configured to receive the proximal end of the invasive medical device, wherein the hub housing comprises at least one integrated circuit embedded therein, the at least one integrated circuit being configured to contact the external surface of the invasive medical device to electrically connect the transducer to a power source, wherein the at least one integrated circuit embedded in the hub housing comprises a molded interconnect device (MID), wherein the body of the MID includes a concave seat in which a portion of the invasive medical device is placed; and
at least one conductive element extending from the transducer to the proximal end electrically connecting the transducer to the at least one integrated circuit of the hub housing.

2. The invasive medical device assembly of claim 1, wherein the at least one integrated circuit embedded in the hub housing is configured to electrically connect the invasive medical device to the power source via a coaxial cable.

3. The invasive medical device assembly of claim 2, wherein the at least one integrated circuit comprises a first conductive region and a second conductive region, the first conductive region configured to electrically connect a first conductor of the coaxial cable to the invasive medical device, and the second conductive region configured to electrically connect a second conductor of the coaxial cable to the invasive medical device.

4. The invasive medical device assembly of claim 1, wherein the at least one conductive element comprises at least one of an electrical trace printed on the external surface of the invasive medical device via an additive manufacturing process, a flexible printed circuit board, an electrically conductive cable, or a combination thereof.

5. The invasive medical device assembly of claim 1, wherein the hub housing encloses a portion of the invasive medical device.

6. The invasive medical device assembly of claim 5, wherein the hub housing further comprises a port configured to receive a cable to electrically connect the at least one integrated circuit to the power source.

7. The invasive medical device assembly of claim 1, wherein the invasive medical device is a needle, a catheter, a stylet, a punch, or an introducer.

8. The invasive medical device assembly of claim 1, wherein the external surface of the invasive medical device is coated with a first electrically insulating material, wherein the at least one conductive element is located over the first electrically insulating material.

* * * * *